US006343109B2

(12) United States Patent
Doubrava et al.

(10) Patent No.: US 6,343,109 B2
(45) Date of Patent: Jan. 29, 2002

(54) CT APPARATUS WITH REDUCED DATA TRANSMISSION RATE FROM THE DETECTOR SYSTEM TO THE IMAGE RECONSTRUCTION COMPUTER

(75) Inventors: Clemens Doubrava, Nuremberg (DE); Guenter Hahn, Shanghai (CN)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/772,139

(22) Filed: Jan. 29, 2001

(30) Foreign Application Priority Data

Jan. 27, 2000 (DE) .......................................... 100 03 518

(51) Int. Cl.[7] ................................................. A61B 6/03
(52) U.S. Cl. ............................... 378/4; 378/15; 378/19; 378/901
(58) Field of Search ............................ 378/4, 15, 19, 378/901

(56) References Cited

U.S. PATENT DOCUMENTS 5,159,551 A * 10/1992 Brunnet et al. ............. 382/131
5,835,559 A   11/1998 Hsieh ............................ 378/4
5,867,555 A    2/1999 Popescu et al. ............. 378/16
2001/0017909  *  8/2001 Doubrava et al. .......... 378/901

FOREIGN PATENT DOCUMENTS

DE   198 54 470   5/1999
JP    09035844    9/1998

* cited by examiner

Primary Examiner—David V. Bruce
(74) Attorney, Agent, or Firm—Schiff Hardin & Waite

(57) ABSTRACT

A CT (computed tomography) apparatus has a detector system which produces an x-ray beam that rotates around a system axis, and which produces data representing attenuation of the x-rays by an examination subject, and a data transmission path for the transmission of data from the detector system to an image reconstruction computer that is stationary relative to the detector system. Data required for a live image are extracted from the data supplied by the detector system during the scanning of a subject under examination, and are transmitted during the scanning to the image reconstruction computer via the data transmission path and after completion of the scanning, all data supplied by the detector system during the scanning are transmitted to the image reconstruction computer.

4 Claims, 2 Drawing Sheets

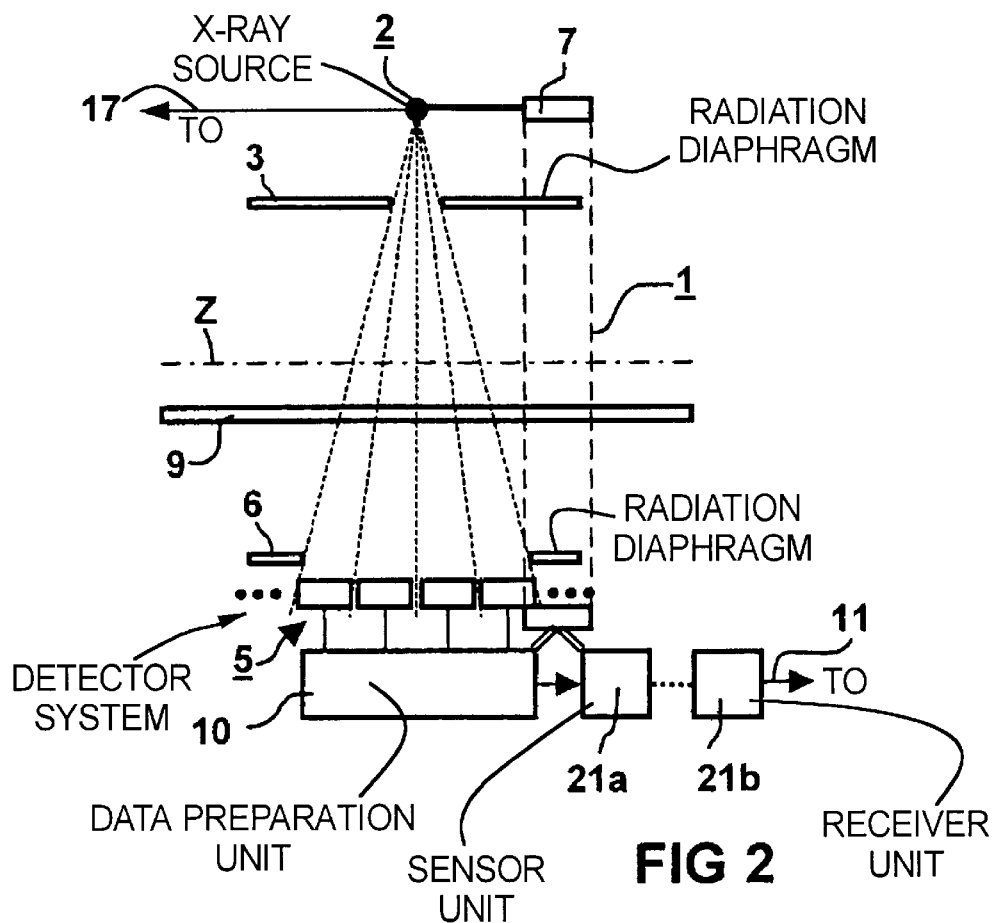
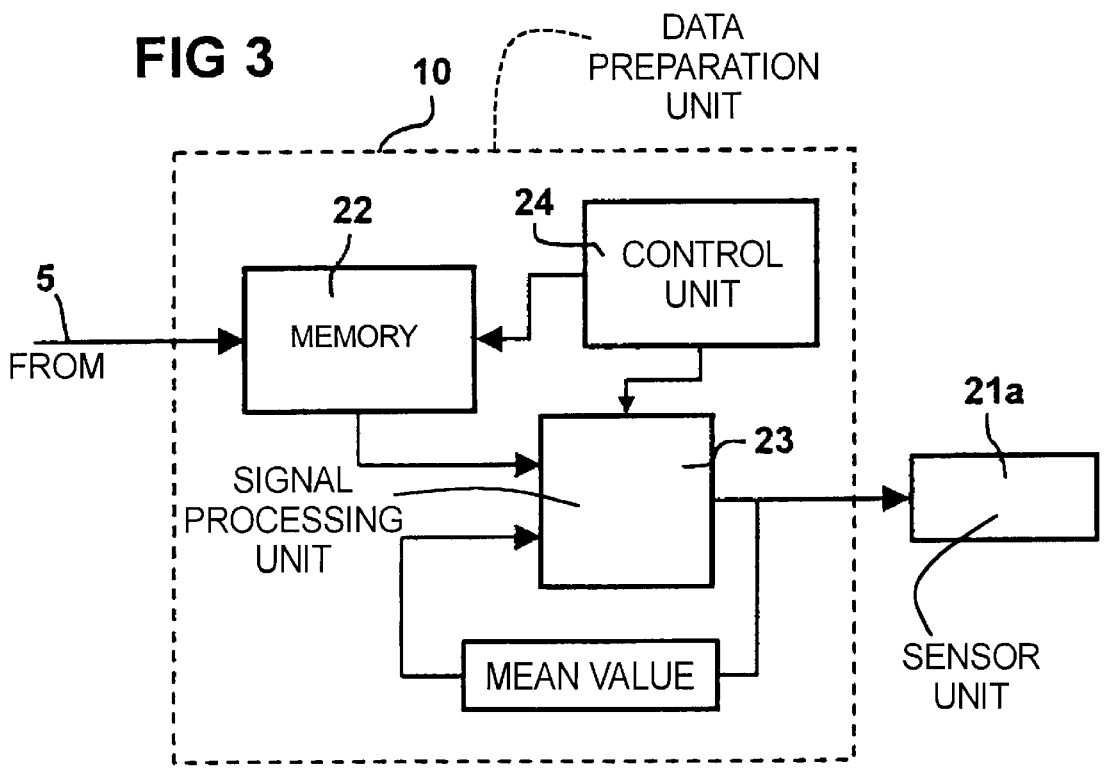

CT APPARATUS WITH REDUCED DATA TRANSMISSION RATE FROM THE DETECTOR SYSTEM TO THE IMAGE RECONSTRUCTION COMPUTER

BACKGROUND OF THE INVENTION

1. Field of the Invention

The present invention relates to a computed tomography (CT) apparatus of the type having a detector system that rotates around a system axis, an image reconstruction computer that is stationary in relation to the detector system, and a data transmission path forth transmission of data from the detector system to the image reconstruction computer, which reconstructs an image from the transmitted data and present this image on a display.

2. Description of the Prior Art

Users of current CT apparatuses as described, for example in Japanese Application 102 29 982, Japanese Application 110 76 226, Japanese Application 112, 35 336 and U.S. Pat. No. 5,867,555, expect a live reconstruction on the monitor, i.e., an image reconstructed and presented on the display (live image) immediately after, or if possible, during, the scanning of a subject under examination using the CT apparatus.

In order to satisfy this expectation, it is necessary that the data supplied by the detector system be transmitted from the rotating detector system to the stationary image reconstruction computer at a data rate that is not lower, or is not significantly lower, than the data rate at which the data are supplied by the detector system.

In particular, in a CT apparatus with a detector system formed by a two-dimensional array of detector elements (known as a multiple-layer CT apparatus), the satisfaction of this requirement encounters difficulties, since the data rate his higher by the same degree as the number of detector elements in relation to a conventional CT apparatus having a one-dimensional array of detector elements (detector row).

SUMMARY OF THE INVENTION

An object of the present invention is to provide a CT apparatus of the type described above wherein a live image can be produced even if the data rate at which the data supplied by rotating detector system are transmitted to the stationary image reconstruction computer is lower than the data at which the data are supplied by the detector system.

This object is achieved in a CT apparatus in accordance with the invention, wherein in a first phase during the scanning of the subject under examination (preferably taking place in the form of a spiral scan), data (in the case of a spiral scan, volume data) are extracted, using the data preparation unit, from the data supplied by the detector system and are transmitted to the image reconstruction computer via the data transmission path during the scanning, the computer reconstructs an image (live image) from the extracted data that provides an operator with preliminary information concerning the results of the examination.

The extracted data can, for example, be produced such that, dependent on the algorithm used for the image reconstruction, the data preparation unit forms the mean value from a number of (preferably successive) partial rotation data sets or complete rotation data sets.

In a second phase, after the completion of the scanning of the subject under examination, all data supplied by the detector system during the scanning are transmitted in unmodified form to the image reconstruction computer via the data transmission path.

Since in the first phase only a small part of the data supplied by the detector system during the scanning of the subject under examination need to be transmitted, and the transmission after the scanning of all the data supplied by the detector system during the scanning of the subject under examination is not time-critical, there are no particular requirements with respect to the data transmission rate of the data transmission path. Thus the requirement of rapid production of a first live image can be fulfilled with comparatively low outlay and without the necessity of the data transmission path operating at a high data rate. Depending on the way in which the extracted data are obtained, for the transmission of the extracted data a data rate is sufficient that is on the order of magnitude of one-fourth of the data rate that would be required for the transmission of all the data during the scanning.

The invention is in particular suitable for multiple-layer CT apparatuses whose detector system is a two-dimensional array of detector elements that are preferably arranged in a number of rows and columns. However, the invention is not limited to CT apparatuses of this sort, but is suitable for CT apparatuses whose detector system is a one-dimensional array of detector elements, such as a detector row.

Moreover, the invention is in particular suitable for CT apparatuses known as spiral CT apparatuses, in which during a scanning a continuous rotation of the detector system about the system axis takes place, with simultaneous displacement of the subject under examination and the detector system relative to one another, in the direction of the system axis. In a CT apparatus of this type, considerable quantities of data can occur during a scanning, whose transmission during the scanning would be problematic without the invention.

DESCRIPTION OF THE DRAWINGS

FIG. 2 shows a longitudinal section through the apparatus according to FIG. 1.

FIG. 3 shows a schematic diagram of the data preparation unit of the CT apparatus according to FIGS. 1 and 2.

DESCRIPTION OF THE PREFERRED EMBODIMENTS

Figure 1:
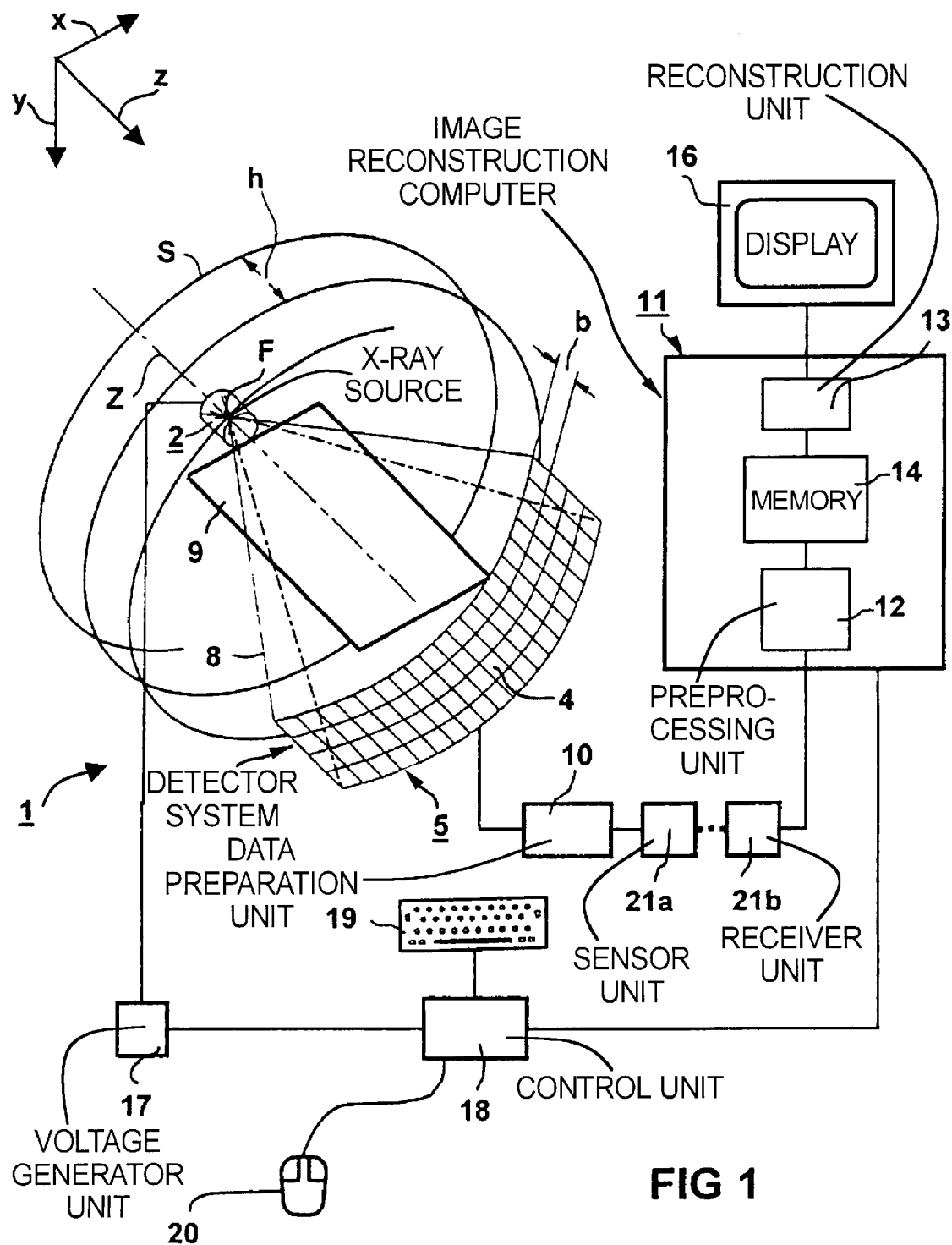
FIG. 1 shows, in a partially perspective and partially schematic representation, a CT apparatus suitable for execution of the inventive method.

FIGS. 1 and 2 show a third-generation multiple-layer CT apparatus that is suitable for the execution of the inventive method. The measurement arrangement, designated generally as 1, has an x-ray source 2, having a beam diaphragm 3 (FIG. 2) positioned in front of and close to the source 2. The measurement arrangement 1 also has a detector system 5, fashioned as a planar array of a number of rows and columns of detector elements (one of these is designated 4 in FIG. 1), with a beam diaphragm 6 (FIG. 2) positioned in front of and close to the system 2. The x-ray source 2 with the beam diaphragm 3, and the detector system 5 with the beam diaphragm 6, are mounted, as shown in FIG. 2, opposite one another on a rotating frame 7 so that a pyramid-shaped x-ray beam bundle that emanates from the x-ray source 2 during operation of the CT apparatus and is gated by the adjustable beam diaphragm 3, and whose edge beams are designated 8, is incident on the detector system 5. The beam diaphragm 6 is set to correspond to the cross-section, using the beam diaphragm 3, of the x-ray beam bundle so that only that region of the detector system 5 that can be immediately struck by the x-ray beam bundle is exposed. In the operating state shown in FIGS. 1 and 2, this corresponds to four rows of detector elements. The fact that additional rows of detector elements are present, that are covered or shielded by the beam diaphragm 6, is indicated by the dots in FIG. 2.

The rotating frame 7 can be displaced rotationally about a system axis designated Z using a drive(not shown). The system axis Z proceeds parallel to the z axis of a rectangular spatial coordinate system shown in FIG. 1.

The columns of the detector system 5 likewise proceed in the direction of the z axis, while the rows, whose width b is measured in the direction of the z axis, and is for example equal to 1 mm, proceed transversely to the system axis Z, or the z axis.

In order to enable a subject under examination, e.g. a patient, to be brought into the beam path of the x-ray beam bundle, a positioning arrangement 9 is provided that can be displaced parallel to the system axis Z, i.e., in the direction of the z axis.

For the acquisition of volume data of a subject under examination located on the positioning arrangement 9, e.g. a patient, a scanning of the subject under examination takes place by recording, with motion of the measurement unit 1 around the system axis Z, a number of projections from various projection directions. The data supplied by the detector system 5 therefore contain a number of projections.

During the continuous rotation of the measurement unit 1 around the system axis Z, the positioning arrangement 9 is simultaneously continuously displaced relative to the measurement unit 1 in the direction of the system axis Z, with a synchronization between the rotational motion of the rotating frame 7 and the translational motion of the positioning arrangement 9, in the sense that the ratio of translational speed to rotational speed is constant. This constant ratio can be adjusted by selecting a value for the advancement h of the positioning arrangement 9 per rotation of the rotating frame 7 that ensures a complete scanning of the volume of interest of the subject under examination. Seen from the subject under examination, the focus F of the x-ray source 2 thus moves around the system axis Z in a spiral path, designated S in FIG. 1, for which reason scanning using this type of acquisition of volume data is known as a spiral scan. The volume data thereby supplied by the detector elements of each row the detector system 5, relating to projections respectively allocated to a particular row of the detector system 5 and to a particular position relative to the system axis Z, are read out in parallel, are serialized in a pre-processing unit 10, and are transmitted to an image reconstruction computer 11 via a data transmission path. The pre-processing unit 10 and a sensor unit 21a of the data transmission path are connected to the rotating frame 7 and follow the motion thereof, which is illustrated by a double connection line to the rotating frame 7. The receiver unit 21b of the data transmission path is, like the image construction computer 11 to which it supplies the received stream of data, stationary relative to the rotating frame 7.

After pre-processing the volume data in the pre-processing unit 12 of the image reconstruction computer 11, the data stream from the receiver unit 21b reaches a memory 14 in which the volume data are stored.

The image reconstruction computer 11 contains a reconstruction unit 13 that reconstructs image data, e.g. in the form of tomograms of desired slices of the subject under examination, from the volume data stored in the memory 14, according to a method known to those skilled in the art. The image data reconstructed by the reconstruction unit 13 are likewise stored in the memory 14 and can be displayed on a display unit 16, e.g. a video monitor, connected to the image reconstruction computer 11.

The x-ray source 2, for example an x-ray tube, is supplied with the necessary voltage and current by a voltage generator unit 17. In order to enable these to be set to the required values, a control unit 18 with a keyboard 19 and mouse 20, permitting the necessary adjustments, are allocated to the generator unit 17.

The remaining operation and control of the CT apparatus also takes place by means of the control unit 18 and the keyboard 19 as well as the mouse 20, which is illustrated by the connection of the control unit 18 with the image reconstruction computer 11.

The volume data available at the output of the detector system 5 are supplied in digital form to the data preparation unit 10, shown in FIG. 3 as a block in broken lines, and these data reach a memory 22 that stores all the volume data that occur during a spiral scan.

During the execution of a spiral scan, a digital signal processing unit 23 extracts, from the volume data located in the memory 22, data that permit the reconstruction of a live image, and transmits the extracted data, via the sensor unit 21a and the receiver unit 21b of the data transmission path, to the image reconstruction computer 11, which reconstructs a live image from the extracted data, and presents this image on the display unit 16.

The data rate at which the data transmission path operates is chosen such that the transmission of the extracted data does not in any case significantly exceed the duration of the spiral scan.

After the completion of the spiral scan, the totality of the data acquired during the spiral scan and recorded in the memory 22 is transmitted in unmodified form, and at the same data rate at which the transmission of the extracted data also took place, from the data preparation unit 10 to the image reconstruction computer 11 via the data transmission path.

In the inventive CT apparatus, the reconstruction of live images is possible without the necessity of the data transmission path operating at a data rate such as would be required for the transmission during the examination of all the data occurring during a spiral scan.

As can be seen in FIG. 3, the cooperation of the memory 22 and the digital signal processing unit 23 of the data preparation unit 10 is controlled by a control unit 24, for example a microcontroller.

The data that reach the memory 22 during a spiral scan from the individual rows of the detector system 5 contain a number of partial rotation data sets, or complete rotation data sets, that are respectively allocated to the individual rows of the detector system 5. A partial rotation data set contains projections that are recorded through a projection angle region (i.e., a rotated angle region of the measurement unit 1) around the system axis Z that is at least equal to the projection angle region required for the reconstruction of a tomogram but is smaller than 360°. A complete rotation data set contains projections that are recorded through a projection angle of at least 360°. In the exemplary embodiment, the extracted data are produced by the digital signal processing unit 23 forming the mean value from a number of partial rotation data sets or complete rotation data sets (e.g., four partial rotation or complete rotation data sets) and transmits the corresponding resulting partial rotation or complete rotation data set to the image reconstruction computer 11 as extracted data. The extracted data can be, depending in particular on the scope and duration of the spiral scan, a single partial rotation data set or complete rotation data set, or can be a number of such sets. In the case of the transmission of a number of data sets, a number of live images can be reconstructed and displayed.

The mean value formation explained above is illustrated in FIG. 3 by a corresponding loop that connects the output and one input of the digital signal processing unit 23 with one another.

As an example, a detector system 5 having 32 rows, having 768 individual detectors, is assumed, and it is further assumed that 1000 projections are recorded per rotation of the rotating frame 7 and per row, then if a rotation of the rotating frame lasts 0.4 sec, given a resolution of 17 bits for the complete transmission of the data supplied by the detector system 5 during a scanning, a data rate of >1.04448 Gbit/sec is required.

In contrast, under the precondition that, for obtaining the extracted data, four partial rotation or complete rotation data sets are averaged and are used as the basis for the reconstruction of a live image, a quarter of the data rate required for the complete transmission is sufficient for the transmission of the extracted data.

For the above parameters, and with the additional assumption of a displacement in the direction of the system axis Z of 200 cm, given 50 rotations of the measurement unit 1 around the system axis Z (pitch 4 cm) a capacity of the memory 22 of approximately 21 Gbytes is required for the storage of all data supplied during a spiral scan by the detector system 5. This capacity can be further reduced by applying any known loss-free compression technique to the volume data.

The production of the extracted data not necessarily take place using mean value formation. Other procedures are possible, such as the transmission during the spiral scan of only each nth partial rotation or complete rotation data set; for example, every eighth partial rotation or complete rotation data set.

In the exemplary embodiment, the design of the image reconstruction computer 11 is described with the preprocessing unit 12 and the reconstruction unit 13 as hardware components. This can in fact be the case. As a rule, however, the se components are realized by software modules that operate on a universal computer provided with the required interfaces, which, differing from FIG. 1, can also take over the function of the control unit 18, which would then be superfluous.

In the exemplary embodiment, the CT apparatus has a detector system 5 having rows whose width, measured in the z direction, are equal in size, measuring for example 1 mm. However, it is also within the scope of the invention to employ a detector system whose rows are of differing widths.

In the exemplary embodiment, the relative motion between the measuring unit 1 and the positioning arrangement 9 is produced by displacing the positioning arrangement 9. However, it is also within the scope of the invention to leave the positioning arrangement 9 stationary and to displace the measurement unit 1 instead. Moreover, it is within the scope of the invention to produce the necessary relative motion by displacing both the measurement unit 1 and the positioning arrangement 9.

A third-generation CT apparatus is described used in connection with the exemplary embodiments, i.e., the x-ray source and the detector system are displaced in common around the system axis during the imaging. However, the invention can also be used in connection with a CT apparatus of the fourth generation, in which only the x-ray source is displaced around the system axis and cooperates with a stationary detector ring, as long as the detector system is a planar array of detector elements.

The inventive method can also be used in a fifth-generation CT apparatus, i.e., a CT apparatus in which x-rays emanate not solely from one focus, but rather from a number of foci of one or more x-ray sources that are distributed around the system axis, as long as the detector system is a planar array of detector elements.

The CT apparatus used in connection with the exemplary embodiments has a detector system with detector elements arranged in the manner of an orthogonal matrix. However, the invention can also be used in connection with a CT apparatus having a detector system with detector elements arranged in another manner in a planar array.

The exemplary embodiments relate to the medical application of the inventive method, however, the invention also can be used outside of medicine, for example, in the examination of luggage or the examination of other materials.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:
   an x-ray source, which generates an x-ray beam that rotates around a system axis;
   a detector system which rotates around said system axis together with said x-ray source and which detects radiation attenuated by an examination subject during scanning of said examination subject and produces data representing the attenuated radiation;
   an image reconstruction computer located remote from said detector system and not rotating with said detector system;
   a data transmission path between said rotating detector system and said image reconstruction computer for transmitting said data from said detector system to said image reconstruction computer;
   a memory allocated to said detector system for storing said data from said detector system and rotating with said detector system;
   a data preparation unit allocated to said detector system which rotates with said detector system and which is connected to said memory, said data preparation unit transmitting said data from said memory to said image reconstruction computer via said data transmission path after completion of the scanning, and said data preparation unit extracting, from the data from the detector system, data transmitted during the scanning to the image reconstruction computer via the data transmission path, as extracted data; and
   a display connected to said image reconstruction computer, said image reconstruction computer reconstructing an image of said examination subject from said extracted data and causing said image to be displayed on said display.

2. A computed tomography apparatus as claimed in claim 1 wherein, during said scanning, a continuous rotation of said detector system occurs around said system axis, and wherein said CT apparatus comprises means for producing relative displacement between said detector system and said examination subject during said scanning.

3. A computed tomography apparatus as claimed in claim 1 wherein said detector system includes a radiation detector formed by a two-dimensional array of detector elements.

4. A computed tomography apparatus as claimed in claim 3 wherein said detector elements are disposed in a plurality of rows and columns, forming a matrix.

* * * * *